United States Patent [19]

Takase

[11] Patent Number: 5,078,724
[45] Date of Patent: Jan. 7, 1992

[54] SCALPEL

[76] Inventor: Haruo Takase, 20-16, 3-chome, Shimoochiai, Shinjuku-ku Tokyo, Japan

[21] Appl. No.: 450,464

[22] Filed: Dec. 14, 1989

[51] Int. Cl.$^5$ .............................................. A61B 17/32
[52] U.S. Cl. ..................... 606/167; 30/351; 30/335; 30/329
[58] Field of Search ................. 606/172, 167; 30/294, 30/351, 340, 339, 329, 335; 128/751-754

[56] References Cited

U.S. PATENT DOCUMENTS

| | | | |
|---|---|---|---|
| 1,287,411 | 12/1918 | Parker | 30/339 |
| 3,490,455 | 1/1970 | Illig | 128/20 |

FOREIGN PATENT DOCUMENTS

| | | | |
|---|---|---|---|
| 1144437 | 2/1963 | Fed. Rep. of Germany | 606/167 |
| 1-64015 | 3/1989 | Japan | |

OTHER PUBLICATIONS

Mueller, "The Surgical Armamentarium", 1980, pp. 2, 3, 5.

Primary Examiner—Michael H. Thaler
Attorney, Agent, or Firm—Oblon, Spivak, McClelland, Maier & Neustadt

[57] ABSTRACT

In a scalpel having a disposable blade and a handle for retaining the blade, the disposable blade is provided on its rear end portion with at least one tongue piece which can be held with a tool such as a needle holder or forceps. The replacement of the blade with another can be easily and promptly carried out while holding the tongue piece with the tool even in the midst of the surgical operation, so that the blades of various types different in shape can be properly used for each purpose.

1 Claim, 2 Drawing Sheets 5,078,724

SCALPEL

BACKGROUND OF THE INVENTION

1. Field of the Invention

This invention relates to a scalpel of a blade-disposable type for use in surgical treatment, and more particularly to an improvement in a scalpel capable of readily and reliably replacing a disposable blade with another.

2. Description of the Prior Art

There has conventionally been used a scalpel or surgical knife comprising a handle 1 having a blade fitting head 2 with an engaging protrusion 3 and a disposable flat blade 5 having an engaging hole 6 which comes in detachable engagement with the aforementioned engaging protrusion 3 as illustrated in FIG. 1. The disposable blade 5 is generally provided on its one side with a blade edge 7. The disposable blades of various types different in blade shape are properly used according to the usage.

The conventional blade for use in a surgical operation is commonly made flat and has blade edge on its one side as specified above. Accordingly, the blade can be adapted to incise or cut straight the tissue of a living body. However, it is unsuitable to incise the tissue in a circle or curve and has a disadvantage that the tissue of the living body is apt to be incised too excess. For instance, a point-like affected part such as a small polyp will not be skillfully cut out with the flat blade as noted above. As a result, the incision performed by use of the flat blade requires much labor and is consequently intended to disfigure the cutis with a scar.

The inventor of this invention has previously proposed a scalpel for the purpose of remedying the shortcoming involved in using the conventional scalpel as mentioned above (Japanese Utility Model Application Public Disclosure SHO 64-46015(A)). The proposed scalpel comprises a handle 11 having a blade fitting head 12 with an engaging protrusion 13, and a disposable blade 15 which is curved laterally so as to assume a semicylindrical or semiconical configuration as illustrated in FIG. 2. The disposable blade 15 has an engaging hole 16 which receives and hooks detachably the engaging protrusion 13 on the blade fitting head 12. The scalpel employing the curved blade 15 entails an advantage that even a small polyp like a point can be skillfully cut out in surgical operation without inflicting an excessive incision on the cutis. Thus, according to the curved blade the scar being left on the cutis as the result of the surgical operation can be made as small as possible. Furthermore, the curved blade can be easily produced at a relatively low cost.

However, since the disposable blade for use in a scalpel is relatively small, the work of replacing the blade with another calls for meticulous care and often becomes onerous. This is because the disposable blade is curved and small so much as to make it difficult to hold the blade even with a forceps or the like. Specifically when attaching or detaching the disposable blade in the midst of the surgical operation, the blade becomes greasy with blood attached thereto.

Under the circumstances, a need has been felt for a scalpel capable of using various disposable blades different in shape according to the application, the condition of the affected parts and so on and easily and promptly replacing the blade with another even in the midst of the surgical operation.

SUMMARY OF THE INVENTION

An object of the present invention is to provide a scalpel capable of promptly and reliably replacing a curved disposable blade in an easy operation.

Another object of the present invention is to provide a scalpel of the type capable of properly using blades each having a suitable shape so that a surgical operation can be effectively performed without inflicting an excessive incision on the cuits or tissue of a living body.

Still another object of the invention is to provide a scalpel which is easy to handle and capable of using disposable blades of various types produced at a relatively low cost.

To attain the object described above according to the present invention there is provided a scalpel comprising a disposable blade curved longitudinally, a handle having a blade fitting head, and engaging means for bringing the blade into detachable engagement with the blade fitting head of the handle, which blade is provided with at least one tongue piece. The tongue piece extends outward from the rear end or at least one side about the rear end portion of the blade, so that the blade can be easily and reliably held with a needle holder, forceps or the like, thereby permitting easy attachment and detachment of the blade relative to the scalpel handle. Thus, according to the scalpel of this invention, the disposable blades different in shape can be properly used with ease for each purpose.

BRIEF DESCRIPTION ON THE DRAWINGS

The other objects and features of the present invention will now be explained in detail with reference to the accompanying drawings, wherein:

FIG. 1 is a perspective view showing a conventional scalpel of a typical blade-disposable type, FIG. 2 is a perspective view showing a prior art scalpel of a blade-disposable type, FIG. 3 is a perspective view showing one preferred embodiment of the scalpel in its disassembled state according to the present invention, FIG. 4 is a perspective view showing the disposable blade used in another embodiment according to the present invention, and FIG. 5 is a perspective view of still another embodiment of the scalpel according to this invention.

DESCRIPTION OF THE PREFERRED EMBODIMENTS

One preferred embodiment of the blade-disposable type scalpel according to this invention will be described hereinafter with reference to FIG. 3.

The scalpel of this embodiment comprises a handle 21 having a blade fitting head 22 extending forward from the leading end of the handle, and a disposable blade 25 to be detachably attached to the blade fitting head 22 of the handle 21.

The disposable blade is curved laterally (in its width direction) so as to assume a substantially semicylindrical shape having a substantially arcuate cross section. The blade supporting surface of the blade fitting head 22 is correspondingly curved in the width direction thereof so as to come in close contact with the inner surface of the curved blade 25. On the opposite portions of the blade fitting head 22 and curved blade 25 there is disposed engaging means for bringing the blade 25 into detachable engagement with the blade fitting head 22.

Figure 1:
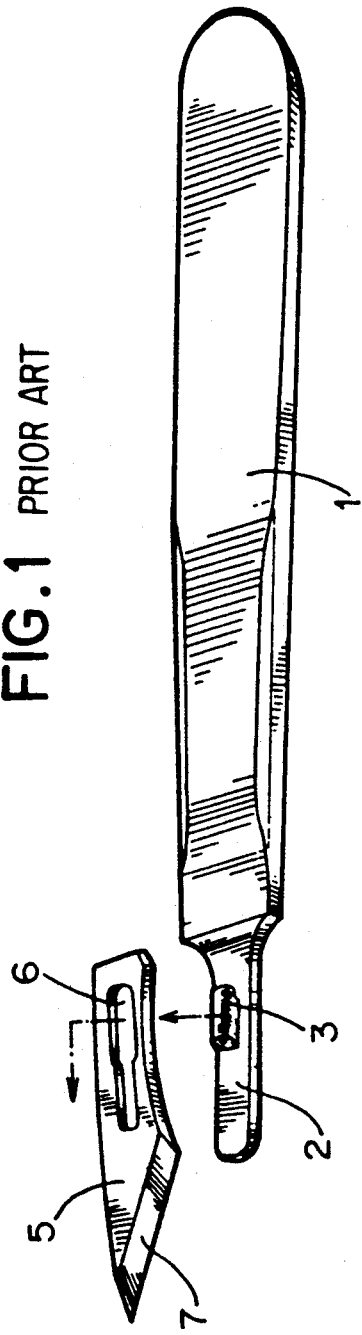
Figure 2:
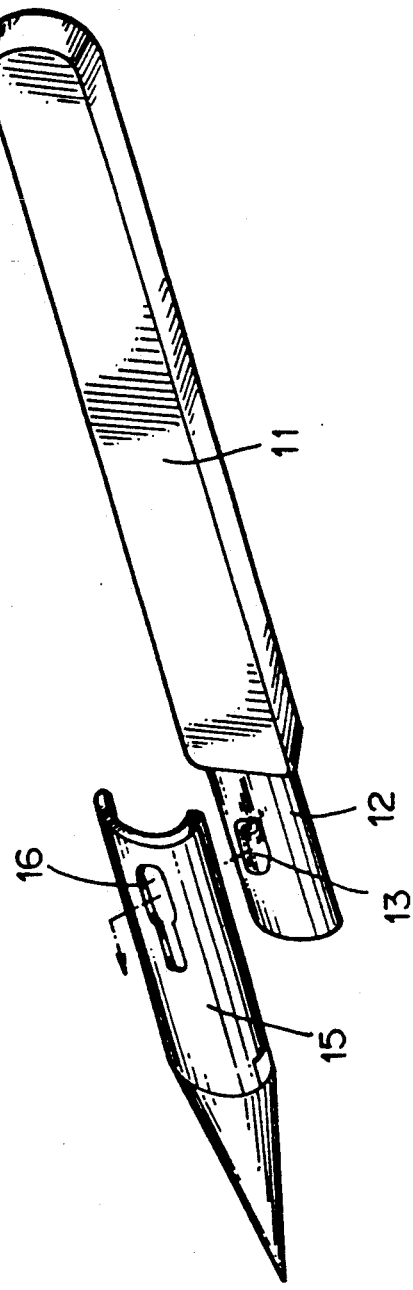
Figure 3:
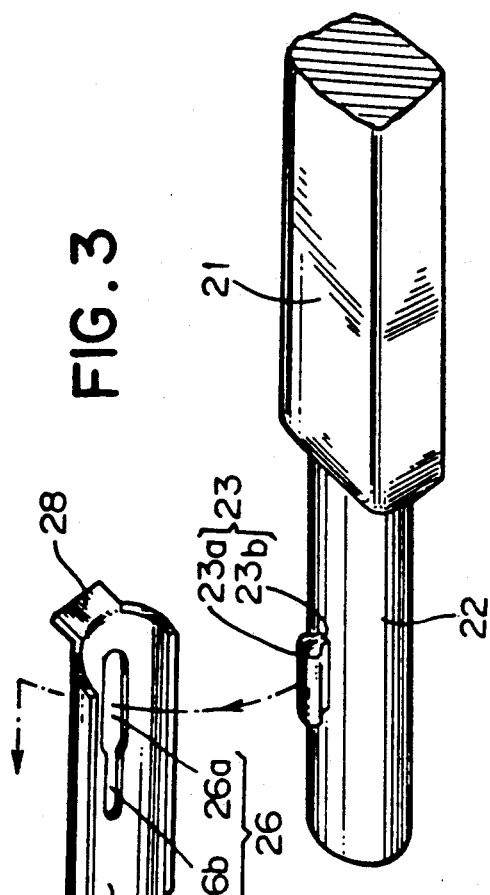

The engaging means in this embodiment comprises, as illustrated in FIG. 3 by way of example, an engaging protrusion 23 having an expanded head portion 23a and a neck portion 23b, which is formed on the blade fitting head 22, and an engaging hole 26 into which the engaging protrusion 23 is inserted so as to be hooked firmly. The engaging hole 26 comprises a larger hole 26a for permitting the expanded head portion 23a of the engaging protrusion 23 to pass therethrough and a smaller hole 26b which is smaller than the expanded head portion 23a and somewhat larger than the neck portion 23b. The holes 26a and 26b are aligned in the lengthwise direction. By first inserting the engaging protrusion 23 into the larger hole 26a and slidably moving the blade 25 so as to place the neck portion 23b in the smaller hole 26b as indicated by the arrow in FIG. 3, the disposable blade 25 can be firmly united with the blade fitting head 22 of the handle 21. It is preferable that the smaller hole 26b be formed on the leading end side and the larger hole 26a be formed on the rear end side as illustrated in order to prevent the blade from accidentally coming off in the midst of the surgical operation. In this case, there should be spaced between the engaging protrusion 23 and the leading end of the handle 21 so as to allow the disposable blade 25 to be slidably move in the longitudinal direction in order for the attachment or detachment.

In the drawing, reference numeral 27 denotes a cutting edge formed on the leading end extending to either side edge of the disposable blade 25.

In the illustrated embodiment, the engaging means is constituted by the engaging protrusion 23 on the blade fitting portion 22 of the handle and the engaging hole 26 in the blade 25; nevertheless, as a countermeasure, the engaging protrusion may be formed on the blade 25 and the engaging hole be formed in the handle 21. Of course, any other structures may be employed as the engaging means.

The disposable blade 25 according to this invention has at least one characteristic tongue piece 28. In the embodiment shown in FIG. 3, the tongue piece 28 extends from a part of the rear end of the blade 25 so that it can be held with a tool (not shown) such as a needle holder and forceps. By holding the tongue piece 28 with the forceps for example, the disposable blade 25 can be easily and reliably attached to or detached from the blade fitting head 22 of the handle 21 without fail.

Figure 4:
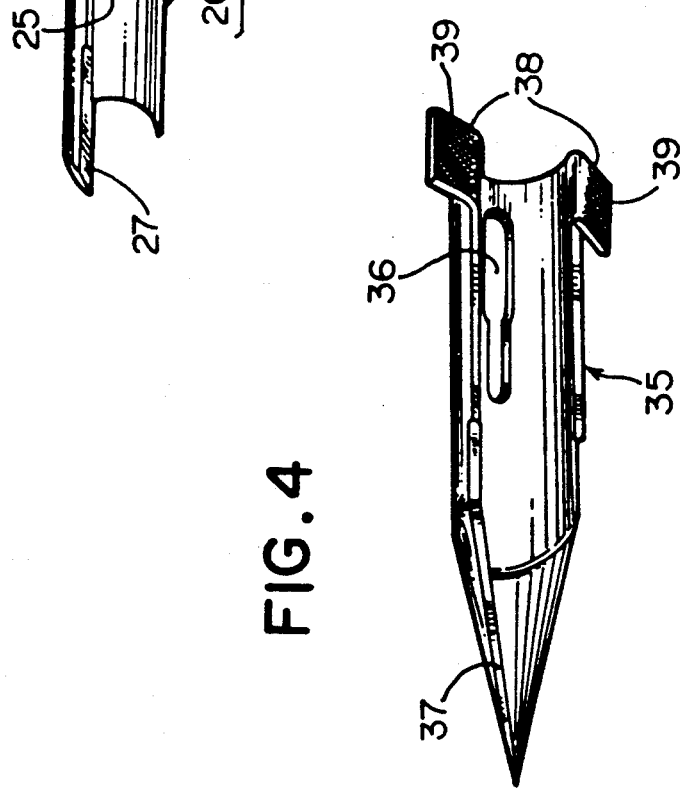

Another embodiment illustrated in FIG. 4 employs a pair of tongue pieces 38 extending one from either side of the rear portion of the blade 35. Although the illustrated blade 35 has two tongue pieces 38, only one tongue piece may be provided on one side of the blade 35. It is desirable to form fine notches 39 one or both surfaces of the tongue piece 38 by knurling and so on, thereby to obtain a sufficiently nonskid effect in holding the tongue piece with a tool such as a forceps.

Though the disposable blade 35 illustrated in FIG. 4 has a tapering leading end portion formed in a substantially conical shape and having cutting edges 37, the shape or configuration of the blade is not specifically limited in this embodiment. To be specific, the degree of the curvature of the blade, the angle of the cutting edge and other design factors should not be understood as limitative.

Reference numeral 36 denotes engaging means for uniting the blade 35 with the handle.

Figure 5:
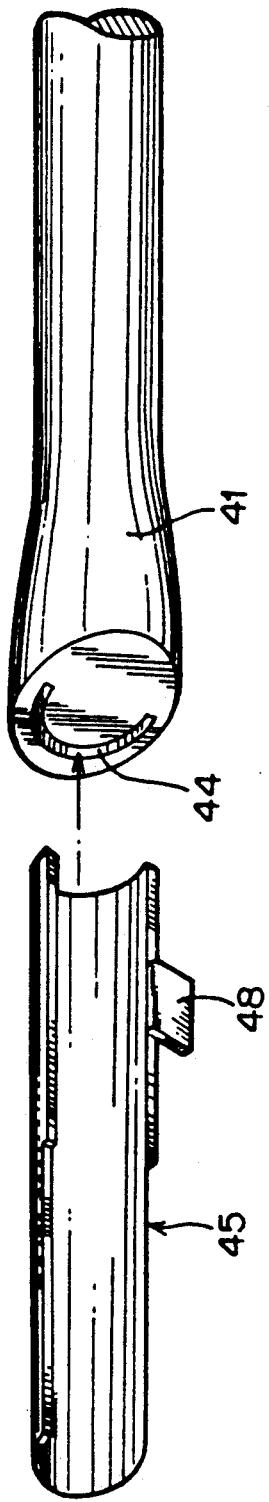

Still another embodiment is illustrated in FIG. 5, in which the engaging means for uniting the blade 45 with the handle 41, is modified. The engaging means is formed of a fitting hole 44 bored in the leading end of the handle 41 and extending in the lengthwise direction of the handle, so that the blade can be inserted in the fitting hole 44. According to this structure of the engaging means, the blade 45 need not be provided with any counterpart of the engaging means. Instead of the fitting hole 44, there may be formed one or more fitting recesses in the leading end surface of the handle 41. The blade 45 is provided with a tongue piece 48 extending laterally from one side portion of the blade. This tongue piece 48 has the same function as those in the foregoing embodiments.

As is apparent from the aforementioned structure, the disposable blade curved laterally, the handle for holding the blade and the engaging means for retaining the blade onto the handle can be modified in various ways within the spirit of this invention. Thus, the invention places no restriction on shapes or structures of the disposable blade and engaging means.

As described above, the scalpel according to this invention permits the work of attaching or detaching the disposable blade to be easily carried out and is easy to handle. Also, since various disposable blades different in shape can be properly used for each purpose in a surgical operation, the cutis and tissue of a living body can be suitably incised or cut out according to the condition of the affected parts without inflicting an excessive incision on the cutis and tissue. Besides, the scalpel of this invention and the disposable blade applicable therefor are very simple in structure and therefore can be easily used and produced at a relatively low cost.

As can be readily appreciated, it is possible to deviate from the above embodiment of the present invention and, as will be readily understood by those skilled in this art, the invention is capable of many modifications and improvements within the scope and spirit thereof. Accordingly, it will be understood that the invention is not to be limited by these specific embodiments, but only by the scope and spirit of the appended claims.

What is claimed is:

1. A scalpel, which comprises:
    a laterally curved disposable blade formed in a substantially semicylindrical shape having a substantially arcuate cross section; and
    a handle having a leading end portion with a fitting hole bored lengthwise therein for permitting said disposable blade to be inserted thereinto, said disposable blade having a rear end portion with at least one tongue piece extending outward for being held with a tool wherein said at least one tongue piece has at least one surface with fine notches formed by knurling.

* * * * *